United States Patent
Vadakkumpadan et al.

(10) Patent No.: US 10,827,983 B2
(45) Date of Patent: Nov. 10, 2020

(54) SYSTEM AND METHOD FOR PERSONALIZED CARDIAC ARRHYTHMIA RISK ASSESSMENT BY SIMULATING ARRHYTHMIA INDUCIBILITY

(71) Applicant: The Johns Hopkins University, Baltimore, MD (US)

(72) Inventors: Fijoy Vadakkumpadan, Baltimore, MD (US); Hermenegild Arevalo, Baltimore, MD (US); Natalia Trayanova, Baltimore, MD (US); Katherine Wu, Bel Air, MD (US)

(73) Assignee: The Johns Hopkins University, Baltimore, MD (US)

( * ) Notice: Subject to any disclaimer, the term of this patent is extended or adjusted under 35 U.S.C. 154(b) by 554 days.

(21) Appl. No.: 13/694,120

(22) Filed: Oct. 30, 2012

(65) Prior Publication Data
US 2014/0122048 A1    May 1, 2014

(51) Int. Cl.
| | |
|---|---|
| *A61B 5/00* | (2006.01) |
| *G06T 7/11* | (2017.01) |
| *G16H 50/30* | (2018.01) |
| *G16H 50/50* | (2018.01) |
| *G16H 30/40* | (2018.01) |
| *A61B 6/00* | (2006.01) |
| *G16H 20/30* | (2018.01) |
| *G16H 20/40* | (2018.01) |

(52) U.S. Cl.
CPC .............. *A61B 5/7275* (2013.01); *G06T 7/11* (2017.01); *G16H 30/40* (2018.01); *G16H 50/30* (2018.01); *G16H 50/50* (2018.01); *A61B 6/503* (2013.01); *G06K 2209/051* (2013.01); *G06T 2207/10088* (2013.01); *G06T 2207/20128* (2013.01); *G06T 2207/30048* (2013.01); *G16H 20/30* (2018.01); *G16H 20/40* (2018.01)

(58) Field of Classification Search
None
See application file for complete search history.

(56) References Cited

U.S. PATENT DOCUMENTS

| | | | |
|---|---|---|---|
| 7,123,953 B2 | 10/2006 | Starobin et al. | |
| 7,421,292 B1 * | 9/2008 | Kroll | 600/518 |
| 2003/0120151 A1 * | 6/2003 | Constantinides | A61K 49/126 600/431 |
| 2004/0215091 A1 * | 10/2004 | Lohman et al. | 600/515 |
| 2005/0018885 A1 * | 1/2005 | Chen | G06T 17/00 382/128 |
| 2010/0191131 A1 * | 7/2010 | Revishvili | A61B 5/04011 600/509 |
| 2011/0087088 A1 * | 4/2011 | Korn | A61B 5/053 600/411 |
| 2011/0087110 A1 * | 4/2011 | Nathan | A61B 5/053 600/476 |
| 2012/0002840 A1 * | 1/2012 | Linnenbank | G06K 9/32 382/103 |
| 2012/0265086 A1 | 10/2012 | Lux | |

OTHER PUBLICATIONS

Trayanova N. Circ Res. Jan. 7, 2011; 108(1): 113-128.*
Constantino et al. Prog Biophys Mol Biol. Oct. 2012; 110(2-3): 372-379.*
Vigmond et al. Exp. Physiol., 94, 563-577, 2009.*
Toussaint et al. Medical Image Computing and Computer-Assisted Intervention—MICCAI 2010. Lecture Notes in Computer Science vol. 6361, 2010, pp. 418-442.*
Saber et al. Annals of Biomedical Engineering, vol. 29, pp. 275-283, 2001.*
Nieman et al. Magn Reson Med. May 2009 ; 61(5): 1148-1157.*
Frangi et al. IEEE Transactions on Medical Imaging, vol. 20, No. 1, 2001, 2-25.*
Helm et al. Ann N Y Acad Sci. 2005; 1047:296-307.*
Aguado-Sierra et al., "Patient-specific modeling of dyssynchronous heart failure: a case study," Progress in Biophysics and Molecular Biology, vol. 107, No. 1, pp. 147-155, 2011.
Albu et al., "A morphology-based approach for interslice interpolation of anatomical slices from volumetric images," IEEE Transactions on Biomedical Engineering, vol. 55, No. 8, pp. 2022-2038, 2008.
Arevalo et al., "Arrhythmogenesis in the Heart: Multiscale Modeling of the Effects of Defibrillation Shocks and the Role of Electrophysiological Heterogeneity," Chaos, vol. 17, No. 1, p. 015103, 2007.
Arevalo et al., "Model of the infarcted canine heart predicts arrhythmia generation from specific cardiac geometry and scar distribution," Heart Rythm, No. 2008.
Ashihara et al., "Tunnel Propagation of Postshock Activations as a Hypothesis for Fibrillation Induction and Isoelectric Window," Circulation Research, vol. 102, No. 6, pp. 737-745, 2008.

(Continued)

*Primary Examiner* — Michael L Borin
(74) *Attorney, Agent, or Firm* — Venable LLP; Henry J. Daley (57) ABSTRACT

A method of determining a likelihood of an occurrence of a cardiac arrhythmia in a patient includes receiving three-dimensional imaging data of said patient's heart, constructing a whole-heart model for simulating at least one of electrophysiological activity or electromechanical activity of the patient's heart using the three-dimensional imaging data, simulating a response of the patient's heart to each of a plurality of stimulations to a corresponding plurality of different locations within the patient's heart using the whole-heart model, classifying each simulation outcome for each stimulation as one of a normal heart rhythm or a cardiac arrhythmia, calculating a likelihood index based on results of the classifying, and determining the likelihood of the occurrence of the cardiac arrhythmia in the patient based on the likelihood index. Software and data processing systems that implement the above methods are also provided.

28 Claims, 8 Drawing Sheets
(6 of 8 Drawing Sheet(s) Filed in Color)

(56) References Cited

OTHER PUBLICATIONS

Bayer et al., "A Novel Rule-Based Algorithm for Assigning Myocardial Fiber Orientation to Computational Heart Models," Annals of Biomedical Engineering, No. p. Published online, 2012.
Beg et al., "Computational Cardiac Anatomy Using MRI," Magnetic Resonance in Medicine, vol. 52, No. 5, pp. 1167-1174, 2004.
Ceritoglu et al., "Multi-contrast large deformation diffeomorphic metric mapping for diffusion tensor imaging," Neuroimage, vol. 47, No. 2, pp. 618-627, 2009.
Chen et al., "Complications of diagnostic electrophysiologic studies and radiofrequency catheter ablation in patients with tachyarrhythmias: an eight-year survey of 3,966 consecutive procedures in a tertiary referral center.," American Journal of Cardiology, vol. 77, No. 1, pp. 41-46, 1996.
Hammill et al., "Review of the Registry's Fourth Year, Incorporating Lead Data and Pediatric ICD Procedures, and Use as a National Performance Measure," Heart Rhythm, vol. 7, No. 9, pp. 1340-1345, 2010.
Hsu et al., "Quantitative myocardial infarction on delayed enhancement MRI. Part I: Animal validation of an automated feature analysis and combined thresholding infarct sizing algorithm," Journal of Magnetic Resonance Imaging, vol. 23, No. 3, pp. 298-308, 2006.
Jie et al., "Mechanisms of mechanically induced spontaneous arrhythmias in acute regional ischemia," Circulation Research, vol. 106, No. 1, pp. 185-192, 2010.
Kels et al., "Reconstruction of 3D objects from 2D cross-sections with the 4-point subdivision scheme adapted to sets," Computers and Graphics, vol. 35, No. pp. 741-746, 2011.
Ng et al., "Virtual Electrophysiological Study in a 3-Dimensional Cardiac Magnetic Resonance Imaging Model of Porcine Myocardial Infarction," Journal of Americal College of Cardiology, vol. xx, No. x, p. Published online, 2012.
Plank et al., "From mitochondrial ion channels to arrhythmias in the heart: computational techniques to bridge the spatio-temporal scales," Philosophical Transactions Series A, Mathematical, Physical, and Engineering Sciences, vol. 366, No. 1879, pp. 3381-3409, 2008.
Raya et al., "Shape-based interpolation of multidimensional objects," IEEE Transactions on Medical Imaging, vol. 9, No. 1, pp. 32-42, 1990.
Relan et al., "Coupled personalization of cardiac electrophysiology models for prediction of ischaemic ventricular tachycardia," Interface Focus, vol. 1, No. 3, pp. 396-407, 2011.
Sermesant et al., "Patient-specific electromechanical models of the heart for the prediction of pacing acute effects in CRT: a preliminary clinical validation," Medical Image Analysis, vol. 16, No. 1, pp. 201-215, 2012.
Soneson et al., "Early changes in the hypothalamic region in prodromal Huntington disease revealed by MRI analysis," Neurobiology of Disease, vol. 40, No. 3, pp. 531-543, 2010.
Stecker et al., "Prediction of sudden cardiac death: next steps in pursuit of effective methodology," Journal of Interventional Cardiac Electrophysiology, vol. 31, No. 2, pp. 101-107, 2011.
Thomas et al., "Electrophysiology Study: Indications and Interpretations," in Management of Cardiac Arrhythmias, G. Yan and P. R. Kowey, Eds., 2 ed: Humana Press, 2011.
Tice et al., "Mechanistic Investigation into the Arrhythmogenic Role of Transmural Heterogeneities in Regional Ischaemia Phase 1a," Europace, vol. 6, No. pp. vi46-vi58, 2007.
Trayanova, "Whole Heart Modeling: Applications to Cardiac Electrophysiology and Electromechanics," Circulation Research, vol. 108, No. pp. 113-128, 2011.
Turk et al., "Shape Transformation Using Variational Implicit Functions," Proc. SIGGRAPH, 1999, pp. 335-342.
Vadakkumpadan et al., "Image-Based Estimation of Ventricular Fiber Orientations for Personalized Modeling of Cardiac Electrophysiology," IEEE Transactions on Medical Imaging, vol. 31, No. 5, pp. 1051-1060, 2012.
Vadakkumpadan et al., "Image-Based Models of Cardiac Structure with Applications in Arrhythmia and Defibrillation Studies," Journal of Electrocardiology, vol. 42, No. 2, pp. 157.e1-157.e10, 2009.
Vadakkumpadan et al., "Left-Ventricular Shape Analysis for Predicting Sudden Cardiac Death Risk," Proc. Engineering in Medicine and Biology Society San Diego, 2012, In press.
Vigmond et al., "Towards predictive modelling of the electrophysiology of the heart.," Experimental Physiology, vol. 94, No. 5, pp. 563-577, 2009.
Wu et al., "Combined Cardiac MRI and C-Reactive Protein Levels Identify a Cohort at Low Risk for Defibrillator Firings and Death," Circulation: Cardiovascular Imaging, vol. 5, No. 2, pp. 178-186, 2012.
Zipes et al., "ACC/AHA/ESC 2006 Guidelines for Management of Patients With Ventricular Arrhythmias and the Prevention of Sudden Cardiac Death a Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death)," Journal of the American College of Cardiology, vol. 48, No. 5, pp. e247-e346, 2006.
Trayanova, N. A., O'Hara, T., Bayer, J. D., Boyle, P. M., McDowell, K. S., Constantino, J., . . . Vadakkumpadan, F. (2012). Computational cardiology: How computer simulations could be used to develop new therapies and advance existing ones. Europace, 14(SUPPL. 5), v82-v8.

* cited by examiner

SYSTEM AND METHOD FOR PERSONALIZED CARDIAC ARRHYTHMIA RISK ASSESSMENT BY SIMULATING ARRHYTHMIA INDUCIBILITY

FEDERAL FUNDING

This invention was made with Government support under Grant Nos. DP1HL123271 and R01HL103428 awarded by the National Institutes of Health (NIH). The Government has certain rights in the invention

BACKGROUND

1. Field of Invention

The field of the currently claimed embodiments of this invention relates to systems and methods for personalized cardiac arrhythmia risk assessment, and more particularly personalized cardiac arrhythmia risk assessment by simulating arrhythmia inducibility.

2. Discussion of Related Art

Sudden cardiac death (SCD) is a leading cause of morbidity and mortality worldwide, with over 300,000 casualties reported annually in the United States alone [1]. Implantable cardioverter-defibrillators (ICDs) have emerged as the most effective preventive treatment for patients at risk, as SCDs typically occur due to ventricular tachycardia (VT) or ventricular fibrillation (VF). However, selection of patients who need ICDs remains challenging [2]. Low left-ventricular ejection fraction (LVEF<35%), the selection criterion commonly used in the current clinical practice, has very low specificity [3]. As such, most of those who currently receive ICDs do not actually benefit from the device. A reduction in the number of such unnecessary implantations will dramatically improve the lives of many, since ICDs are expensive [2], and associated with serious side effects, such as procedural complications, low quality of life, and device malfunctions [3]. Given the current emphasis on reducing health care costs and optimizing therapy, the need for better diagnostic approaches to accurately select patients for ICD implantations is urgent.

Among alternative approaches that have been proposed to further improve patient selection [2], ventricular arrhythmia inducibility during invasive electrophysiological study (EPS) has been exhibited remarkable efficacy [4], and is being recommended by some clinicians [4]. But the applicability of EPS has been limited by its invasiveness [4], expense, and procedural risks [5], especially in the elderly. Therefore, there remains a need for an alternative to clinical arrhythmia inducibility testing.

SUMMARY

A method of determining the likelihood of an occurrence of a cardiac ventricular arrhythmia in a patient according to an embodiment of the current invention includes receiving three-dimensional imaging data of said patient's heart, constructing a whole-heart model for simulating at least one of electrophysiological activity or electromechanical activity of the patient's heart using the three-dimensional imaging data, simulating a response of the patient's heart to each of a plurality of stimulations to a corresponding plurality of different locations within the patient's heart using the whole-heart model, classifying each simulation outcome for each stimulation as one of a normal heart rhythm or a cardiac arrhythmia, calculating a likelihood index based on results of the classification, and determining the likelihood of the occurrence of the cardiac arrhythmia in the patient based on the likelihood index.

A computer-readable medium for determining a likelihood of an occurrence of a cardiac arrhythmia in a patient according to an embodiment of the current invention includes non-transitory computer-executable code. The non-transitory computer-executable code, when executed by a computer, causes the computer to receive three-dimensional imaging data of the patient's heart, construct a whole-heart model for simulating at least one of electrophysiological activity or electromechanical activity of the patient's heart using the three-dimensional imaging data, simulate a response of the patient's heart to each of a plurality of stimulations to a corresponding plurality of different locations within the patient's heart using the whole-heart model, classify each simulation outcome for each stimulation as one of a normal heart rhythm or a cardiac arrhythmia, calculate a likelihood index based on results of the classifying, and determine the likelihood of the occurrence of the cardiac arrhythmia in the patient based on the likelihood index.

A system for determining a likelihood of an occurrence of a cardiac arrhythmia in a patient includes a data processor. The data processor is configured to receive three-dimensional imaging data of the patient's heart, construct a whole-heart model for simulating at least one of electrophysiological activity or electromechanical activity of the patient's heart using the three-dimensional imaging data, simulate a response of the patient's heart to each of a plurality of stimulations to a corresponding plurality of different locations within the patient's heart using the whole-heart model, classify each simulation outcome for each stimulation as one of a normal heart rhythm or a cardiac arrhythmia, calculate a likelihood index based on results of the classifying, and determine the likelihood of the occurrence of the cardiac arrhythmia in the patient based on the likelihood index.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Inducibility of ventricular arrhythmias in clinical electrophysiology study (EPS) has been used for risk stratification of sudden cardiac death (SCD). However, clinical EPS is invasive, expensive, and risky, limiting its applicability. According to some embodiments of the current invention, we have developed a novel methodology to assess arrhythmia inducibility of a patient in silico. Patient-specific computer models of the heart are generated from clinical images, and simulations of programmed electrical stimulation are conducted with these models to induce arrhythmias. The inducibility so assessed can be utilized to stratify the SCD risk of the patient, and to determine if the patient needs an implantable cardioverter defibrillator (ICD).

Implantation of a cardioverter-defibrillator (ICD) is the most effective measure for preventing lethal arrhythmias in patients with myocardial infarction. However, the selection of patients who would benefit from ICD remains very challenging. The typical selection criterion, left-ventricular ejection fraction (LVEF)<35%, has low specificity. Only 5% of patients who meet this criterion and thus undergo device implantation receive life-saving appropriate defibrillation shocks; in the remaining cases the device either never fires or delivers inappropriate shocks due to component malfunction. Given that up to 141,000 patients receive ICDs yearly in the US alone, with each implant costing about $30,000, a more specific criterion that will result in the elimination of unnecessary ICD implantations will bring enormous economic benefit to society. More importantly, defibrillation shocks are associated with a host of adverse effects that include cellular injury, mechanical dysfunction, increased mortality in heart failure patients, and psychological trauma. By eliminating unnecessary implantations, the likelihood of inappropriate shocks and the associated side effects may be drastically reduced, bringing incalculable benefits to many.

Among the alternative criteria that have been proposed to improve ICD selection in patients with infarction, the ability to induce arrhythmia, as probed during a clinical electrophysiological study, has exhibited remarkable efficacy. This approach relies, however, on invasive and protracted point-by-point mapping of electric signals used to determine the ablation targets for infarct-related VT; the applicability of this approach is very limited due to overwhelming limitations. According to some embodiments of the current invention, we use personalized simulations of arrhythmia inducibility in a modeling environment we term "virtual electrophysiological lab" as a noninvasive, inexpensive, and risk-free surrogate for a clinical electrophysiological study to predict lethal arrhythmia risk in patients with low LVEF. The results of the in-silico VT inducibility tests are combined into a new index and used to stratify risk of arrhythmias by means of personalized simulation, thus radically changing the process of patient selection for ICD implantation.

Correlation Between Arrhythmia Inducibility and SCD Risk

It has been known for decades that inducible VT in clinical EPS predicts arrhythmic events [4]. If VT can be induced in a patient's heart with programmed electrical stimulation (PES), typically delivered to the right-ventricular (RV) apex or outflow tract via a catheter, the patient is considered to be at high risk for developing spontaneous arrhythmias. Recent data from the Multicenter Unsustained Tachycardia Trial (MUSTT) and Multicenter Automatic Defibrillator Implantation Trial II (MADIT II), two large clinical trials, conclusively demonstrated that VT inducibility can predict SCD risk in patients with ICM and low LVEF [4]. Specifically, data from MUSTT suggested that the 5-year rate of cardiac arrest and arrhythmic death was 24% in noninducible patients, and 32% in inducible patients [4]. Similarly, MADIT II data indicated that, in patients with ICM and reduced LVEF, 29% of those who met a "standard" definition of inducibility experienced spontaneous VTs during follow up, compared with 19.3% of noninducible patients [4]. These results have led to the current American Heart Association (AHA) Class IIa recommendation that VT inducibility in clinical EPS is reasonable test for SCD risk stratification in patients with remote myocardial infarction, non-sustained VT, and decreased LVEF [1]. However, clinical EPS is invasive, and expensive, requiring the patient to spend several hours in the operating room with specialized personnel. Studies have also revealed significant risks associated with clinical EPS, especially in the elderly, where the complication rate has been shown to be 4-5 times higher [5]. For these reasons, the applicability of clinical EPS remains limited. A very recent study has demonstrated the feasibility of noninvasively reproducing clinical EPS results with in silico models [6]. But this study was performed on a small sample of pigs, and the models lacked crucial anatomic details such as right ventricle (RV) and fiber orientations [6].

Image-Based, Patient-Specific Modeling of the Heart

The heart has become the most advanced example of a virtual organ [7]. Among the various models of the heart, the most detailed ones are based on recent advances in imaging, including ex vivo structural and diffusion tensor (DT) magnetic resonance imaging (MRI), that facilitate acquisition of the intact geometry and myocyte orientations of explanted hearts with hitherto unavailable resolution [8]. These highly detailed models are being used in basic research to uncover specific mechanisms of heart dysfunction in diseases such as ischemic cardiomyopathy (ICM). The potential utility of heart models in aiding diagnosis and optimizing therapeutic interventions has been recognized, and accordingly, efforts to translate the ex vivo image-based modeling approaches to the clinical setting have been undertaken. Relan et al. constructed a personalized model of cardiac electrophysiology of a non-ICM patient, based on late gadolinium enhanced cardiac magnetic resonance (LGE-CMR) images, and electrophysiological data from non-contact mapping [9], and demonstrated that the model can be used for simulation studies of VT induction. The cardiac fiber orientations in this model were estimated from an atlas heart using tools of computational anatomy [10], an emerging discipline that offers rigorous mathematical and algorithmic techniques for the description, transformation, comparison, and statistical inference regarding image-based cardiac geometry. The LGE-CMR images used in this study facilitated the extraction and incorporation of infarct border zone (also known as peri-infarct zone or heterogeneous zone), which is believed to be the anatomical substrate for arrhythmias in ICM patients. In addition, two recent studies, one by Sermesant et al. and the other by Aguado-Sierra et al., have illustrated the generation of patient-specific models of cardiac electromechanics [11, 12]. The former used anatomical data extracted from LGE-CMR, whereas the latter was based on two-dimensional (2D) echocardiographic recordings. While these studies have highlighted the feasibility of building image-based, patient-specific models of the heart, they required invasive techniques such as catheter-based mappings [9, 11, 12], used simplified techniques [9], employed a coarse ventricular geometry [12], or tested the methods on only one or two patients [9, 11, 12].

An embodiment of the current invention can provide a new noninvasive, economical, risk-free in-silico VT inducibility index, which can specifically predict SCD risk in patients with Ischemic Cardiomyopathy (ICM) and reduced LVEF. Ischemic cardiomyopathy (ICM) refers to having an infarction. In some embodiments we can do the same with patients with fibrosis. In further embodiments we can do the same with patients with heart failure. The index can be applied to many patients who are unable to undergo clinical EPS, and provide a new approach to reduce the number of unnecessary ICD implantations. This novel inducibility index can stratify, for the first time, risk of arrhythmias in patients by means of simulations. Given that over 140,000 patients receive ICDs yearly in the US alone based on LVEF [13], embodiments of the current invention can have a dramatic personal, medical, and economic impact on the lives of many. Application of methods according to some embodiments of the current invention in the clinic may shift the current paradigm of SCD risk stratification.

Segmentation of 2D Slices in LGE-CMR Images

Figure 1A:
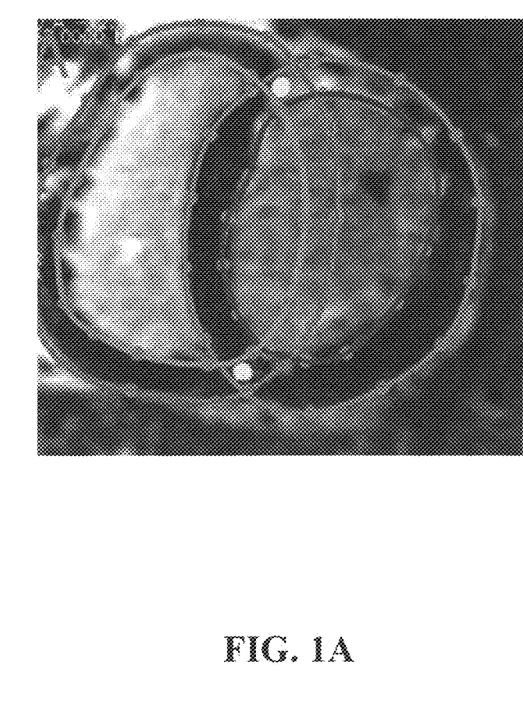
FIGS. 1A and 1B show segmentation of a 2D late gadolinium enhancement cardiac MR (LGE-CMR) slice of an example patient's heart according to an embodiment of the current invention. (A) Labeling of left ventricle (LV) endocardial (blue), LV epicardial (red), right ventricle (RV) endocardial (cyan), RV epicardial (magenta), and RV insertion points (yellow) in each 2D slice. (B) Delineation of core (red) and border (yellow) zones in each 2D slice. The complete 3D reconstruction of LV and infarct geometry from the segmentations shown in (A) and (B) is illustrated in FIG. 2.
Figure 1B:
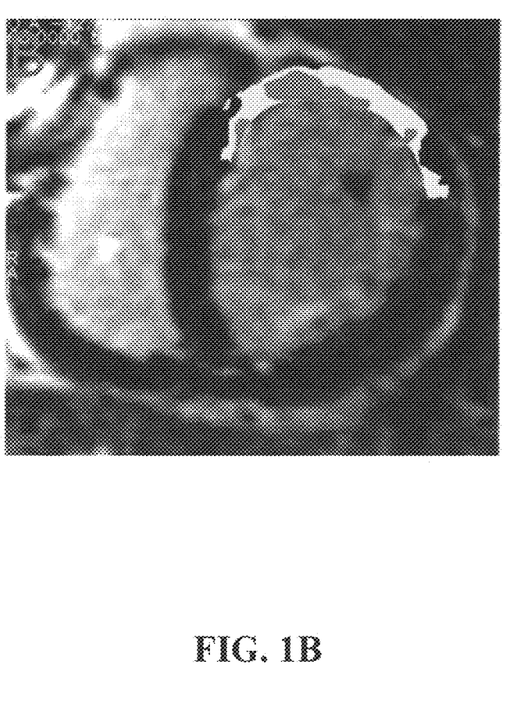

The first step in the generation of patient-specific ventricular models to perform the in-silico VT inducibility tests according to some embodiments of the current invention can is the identification of relevant myocardial tissue regions in the LGE-CMR image, via image segmentation. The inventors have built a software suite to perform this segmentation, and its application to an example LGE-CMR image is illustrated in FIGS. 1A and 1B. As the figure shows, the segmentation involves contouring of endo- and epicardial boundaries, labeling of RV insertion points, and extraction of infarct and/or fibrotic regions.

Note that the infarct region is further divided into core and border zones. The contours are smooth, and the complex geometry as well as interpenetration of core and border zones is captured. Papillary muscles and endocardial trabeculations can be excluded during the contouring. However, they can be kept in other embodiments.

Reconstruction of 3D Ventricular and Infarct Geometries

Figure 2:
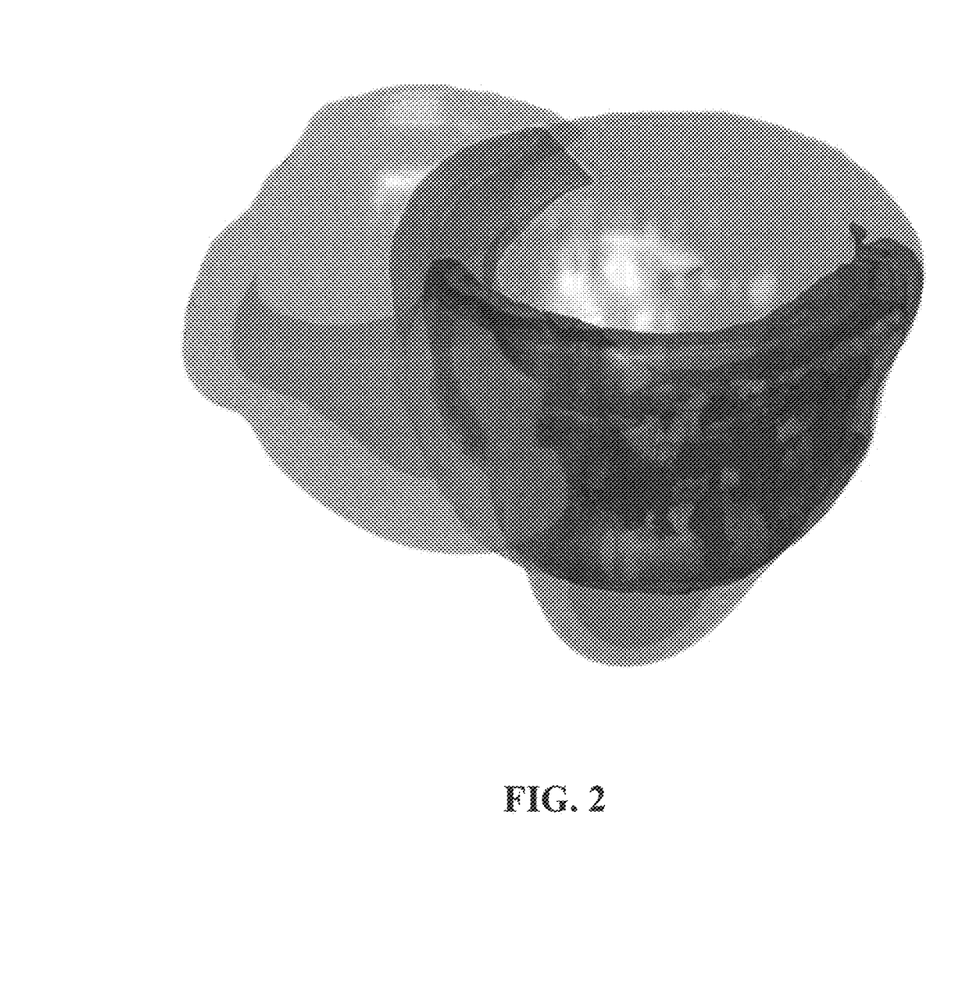
FIG. 2 shows reconstruction of high-resolution 3D patient-specific geometry of the heart from a clinical LGE-CMR image, showing LV free wall (transparent green), RV free-wall (cyan), septum (magenta), infarct core (red), and infarct border zone (blue), according to an embodiment of the current invention.
Figure 8:
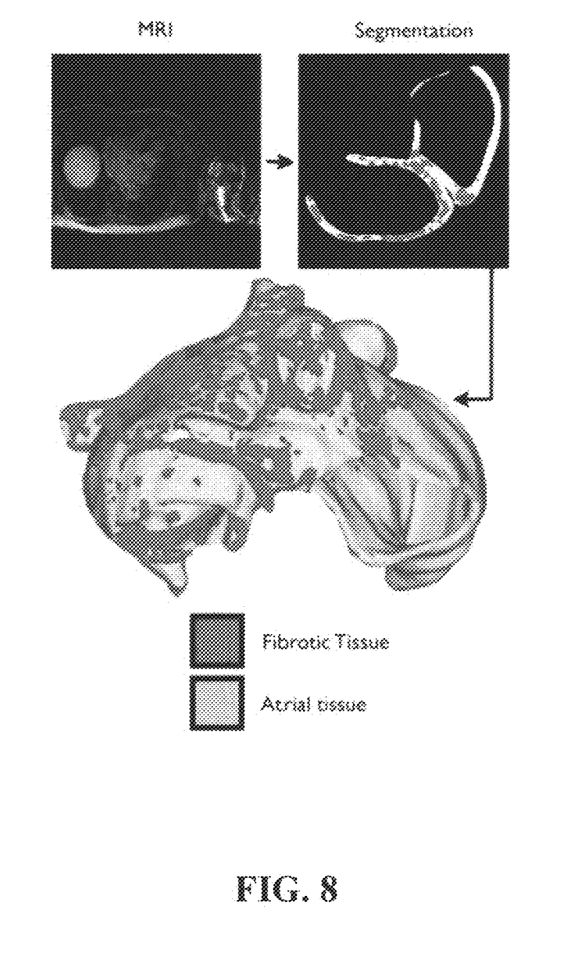
FIG. 8 shows segmentation of fibrotic tissue, according to an embodiment of the current invention.

Tools have been implemented to reconstruct high-resolution (<=1 mm isotropic) 3D geometry of patient ventricular structures and infarct regions and of patient atria and ventricles with fibrosis (or distributed scar) from low resolution (~2×2×10 mm³) clinical LGE-CMR images according to an embodiment of the current invention. The reconstruction involves semi-automatic segmentation of individual 2D LGE-CMR slices, and shape-based interpolation of the segmented data. The reconstruction tools have been applied to several hearts according to an embodiment of the current invention, and an example reconstruction is shown in FIGS. 2 and 8. It is evident from FIGS. 2 and 8 that the tools smoothly generate the data between slices, In the case of FIG. 2 the tools extrapolate beyond the most apical slice in the images so as to fill in the LV apex data that the low-resolution clinical LGE-CMR images do not typically capture. FIGS. 2 and 8 also demonstrate the complex 3D geometries as well as the intermingling of the reconstructed infarct and fibrotic regions. The reconstructions incorporate separate labels for LV free-wall, RV free-wall, septum, infarct core zone, infarct border zone, atria, and fibrotic tissue. Note that the scar core zone in FIG. 2 appears much smaller than it actually is because it is partly hidden by the border zone. Based on experiments with alternative techniques for interpolation, including cubic splines, spherical harmonics, and cylindrical harmonics, we have found that the methodology known as the variational implicit functions scheme [15] outperforms the others in terms of accuracy of fit and smoothness of interpolation.

Construction of Atlas Geometry and Fiber Orientations

Figure 3A:
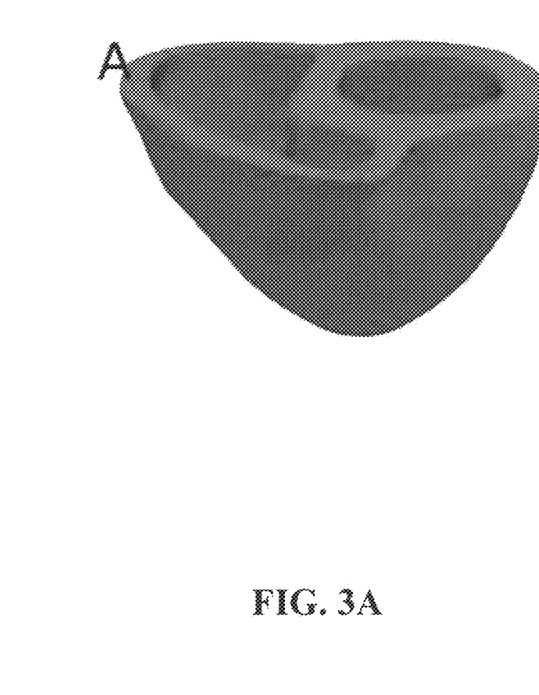
FIGS. 3A and 3B show the geometry (A) and streamlined visualization of fiber orientations (B) of the atlas heart, according to an embodiment of the current invention.
Figure 3B:
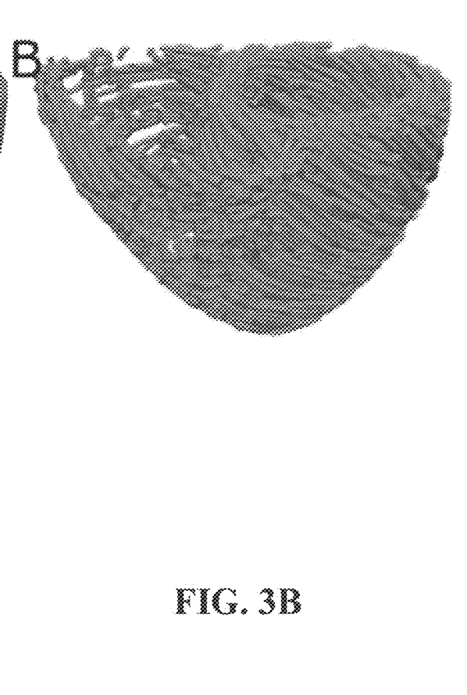
Figure 4A:
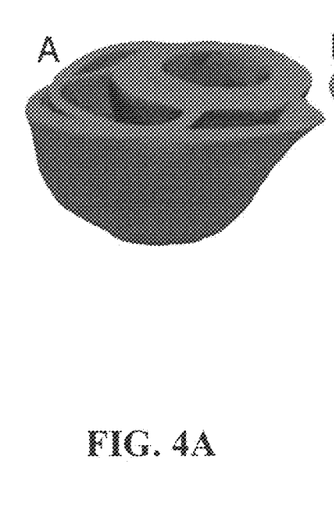
FIGS. 4A-4D show results of the fiber orientations estimation methodology applied to an example patient heart geometry reconstructed from LGE-CMR image. (A) Patient (red) and atlas (magenta) geometries superimposed on each other. (B) Patient geometry and affine transformed atlas geometry. (C) Patient geometry and atlas geometry after MC-LDDMM transformation. (D) Streamlined visualization of the estimated patient fiber orientations, according to an embodiment of the current invention.
Figure 4B:
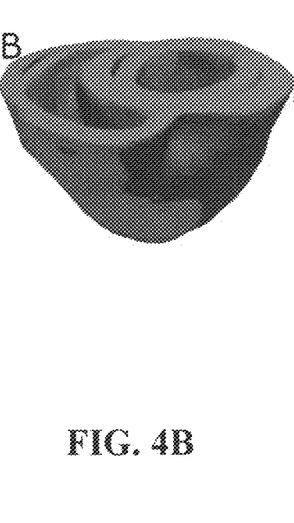
Figure 4C:
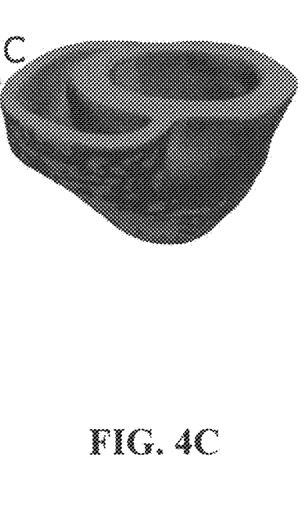
Figure 4D:
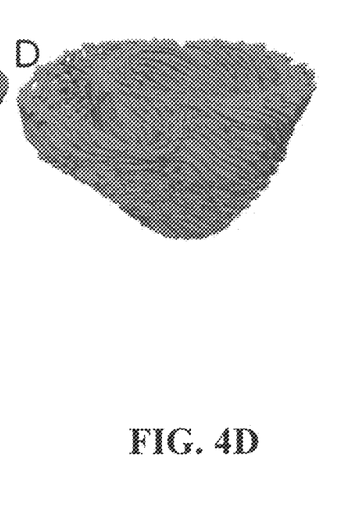

Atlas heart geometry and fiber orientations have been generated according to some embodiments of the current invention to be used for automatic placement of PES sites and estimation of fiber orientations in the patient-specific models. FIG. 3 displays 3D atlas heart geometry and fiber orientations according to an embodiment of the current invention. These atlas data were derived from a high-resolution ex vivo DTMR image of a normal human heart [14].

Estimation of Patient-Specific Ventricular Fiber Orientations

Creation of a patient-specific computational model of the heart requires the acquisition of the patient heart fiber orientations according to an embodiment of the current invention. However, there is no practical method to noninvasively acquire the fiber orientations. To address this need, a novel methodology to estimate the fiber orientations of a patient heart using the patient heart geometry acquired in-vivo has been developed according to an embodiment of the current invention [14]. Given an atlas human heart, for which both geometry and fiber images are available, and a patient heart, for which only the geometry image is available, the methodology uses affine transformation and a high-dimensional, non-linear registration algorithm called multi-channel large deformation diffeomorphic metric mapping (MC-LDDMM), to deform the atlas image such that the deformed geometry image matches the patient geometry image. The deformation field computed in this process is then applied to the atlas fiber orientations to obtain an estimate of the patient heart fiber orientations. FIG. 4 illustrates the application of this methodology to estimating the fiber orientations in an example patient heart. The accuracy of the fiber estimation methodology is assessed by comparing the estimated fiber orientations with those derived from DTMRI. In this assessment, the mean absolute difference between inclination angles of acquired and estimated fiber orientations was 15.4°. Computational simulations of ventricular activation maps and pseudo-ECGs in sinus rhythm and VT indicated that there are no significant differences between estimated and acquired fiber orientations at a clinically observable level. For additional details this fiber estimation methodology and its validation, see also [14].

In Silico Arrhythmia Inducibility Tests

Figure 5:
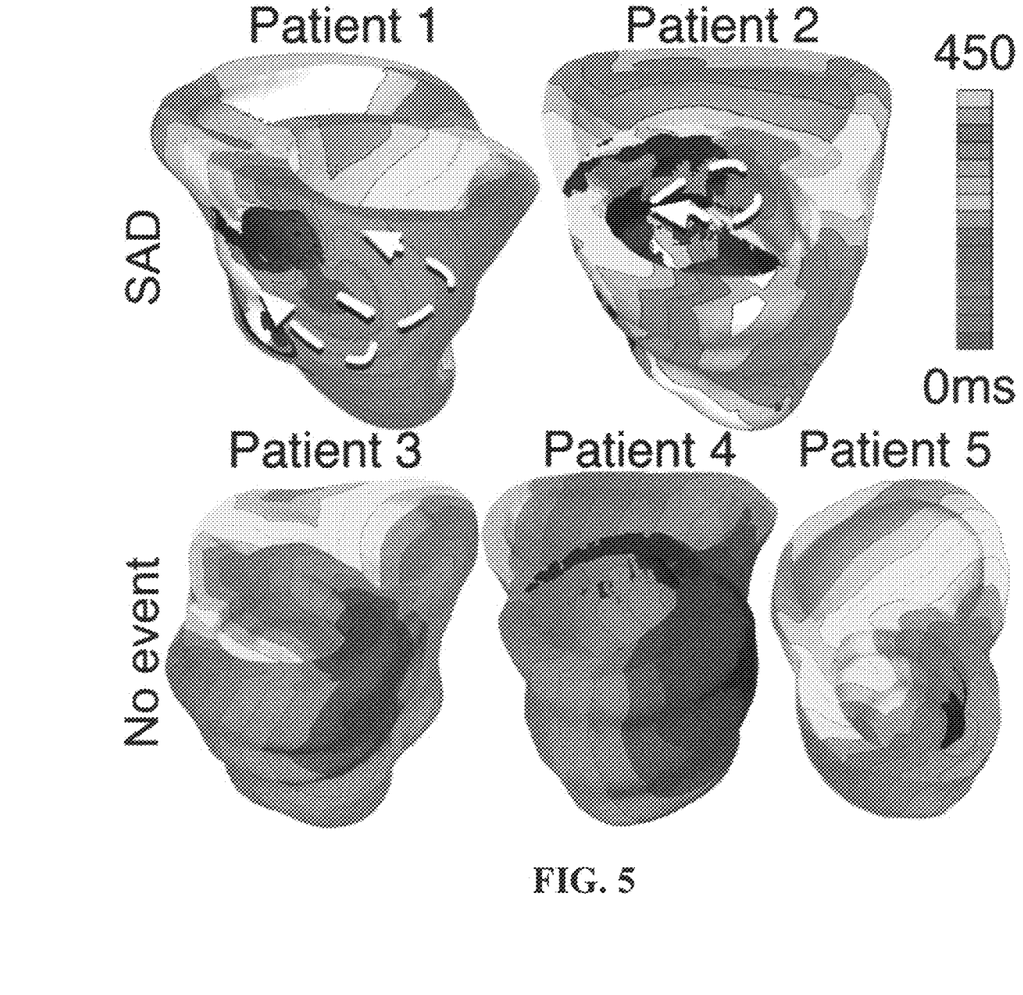
FIG. 5 shows differences in in silico VT inducibility between high-risk (sudden arrhythmic death (SAD), top row) and low-risk (no arrhythmic event, bottom row) patients, according to an embodiment of the current invention. Panels show activations maps after programmed electrical stimulation (PES) from the site in American Heart Association (AHA) region 5, the left-ventricular (LV) posterior base. VT was induced only in the high-risk patients. The in silico VT inducibility index (section 4.1.8) was 3/19 and 8/19 for Patients 1 and 2, respectively, and 0 for others. The white arrows in top panels indicate reentry circuits.

Using tools to construct patient-specific ventricular models of cardiac electrophysiology and perform in silico VT inducibility tests, we conducted tests of VT inducibility on patients with ICM who were imaged with clinical LGE-CMR at the time of ICD insertion, and followed for events, including appropriate ICD firing and sudden arrhythmic death (SAD). FIG. 5 shows the results for five of them. Out of the 5, 2 died of SAD, and therefore were at high risk. The others had no arrhythmic events, including ICD firing or SAD, during follow-up, and so were at a low risk. Ventricular electrophysiological models of each of the patients were constructed and in silico VT inducibility tests were conducted via programmed electrical stimulation (PES) from numerous sites. The simulation results perfectly correlated with clinical follow up data for all the patient-specific models. For the data shown in FIG. 5, the in-silico tests showed no VT induction in the 3 low-risk patients, while they found inducible VTs from multiple sites in the 2 high-risk patients. FIG. 5 illustrates activations maps of PES from the site in AHA region 5 (the LV posterior base) in the 5 patients. In these patient-specific hearts, VT was induced from AHA regions 5, 9, and 11 in Patient 1, and from regions 1, 2, 4, 5, 7, 12, 14, and 16 in Patient 2. Accordingly, the in-silico VT inducibility index, the proportion of PES sites from which VT is induced, was 3/19 and 8/19 for Patients 1 and 2, respectively, and 0 for others. These results are in agreement with prior research which proved that clinical VT inducibility is a predictor of SAD. Moreover, they support the hypothesis according to an embodiment of the current invention that in silico arrhythmia inducibility differs between patients with a low risk of SAD and those with a high risk.

Figure 6:
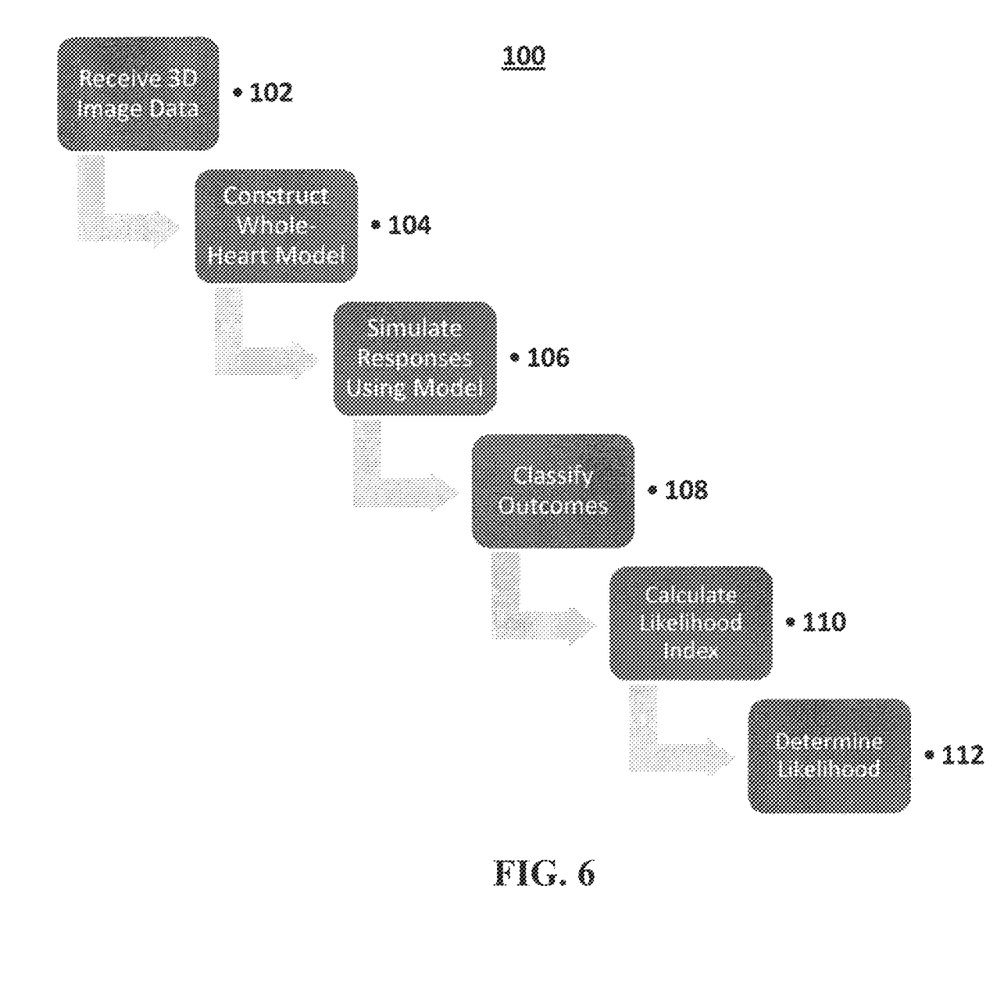
FIG. 6 is a flow chart illustrating a method of determining a likelihood of an occurrence of a cardiac arrhythmia in a patient, according to an embodiment of the current invention.

FIG. 6 is a flowchart illustrating a method 100 of determining a likelihood of an occurrence of a cardiac arrhythmia in a patient according to an embodiment of the current invention. The method 100 includes receiving three-dimensional imaging data 102 of the patient's heart, constructing a whole-heart model 104 for simulating at least one of electrophysiological activity or electromechanical activity of the patient's heart using the three-dimensional imaging data, simulating a response of the patient's heart 106 to each of a plurality of stimulations to a corresponding plurality of different locations within the patient's heart using the whole-heart model, classifying 108 each simulation outcome for each stimulation as one of a normal heart rhythm or a cardiac arrhythmia, calculating a likelihood index 110 based on results of the classifying, and determining the likelihood 112 of the occurrence of the cardiac arrhythmia in the patient based on the likelihood index.

The calculating said likelihood index 110 can be calculating a ratio of number of simulation outcomes resulting in a classification of cardiac arrhythmia divided by total number of simulation outcomes, for example. The determining the likelihood 112 of the occurrence of the cardiac arrhythmia in the patient can include comparing the likelihood index to a predetermined threshold in some embodiments of the current invention.

The plurality of stimulations can be electrical stimulations, as simulated, according to some embodiments of the current invention. The three-dimensional imaging data can be at least one of magnetic resonance imaging (MRI), computed tomography (CT), positron emission tomography (PET), ultrasound, or nuclear tracer three-dimensional imaging data, for example. The method 100 can further include receiving additional patient-specific data that includes at least one of biopsy data, electrocardiogram data, recorded data from an implantable device, or invasive electrical mapping data, according to some embodiments of the current invention, and the simulating 106 can use the additional patient-specific data.

The constructing the whole-heart model 104 of the patient's heart can include constructing a whole-heart geometric model of the patient's heart (see FIG. 7), the whole-heart geometric model including normal tissue regions and remodeled tissue regions determined for said patient using said three-dimensional imaging data. The remodeled tissue regions can include at least one of infarction or fibrosis. FIG. 8 shows an example of fibrosis segmented using imaging data.

The constructing the whole-heart model 104 of the patient's heart can further include estimating tissue fiber orientations in the whole-heart geometric model of the patient's heart.

EXAMPLES

Figure 7:
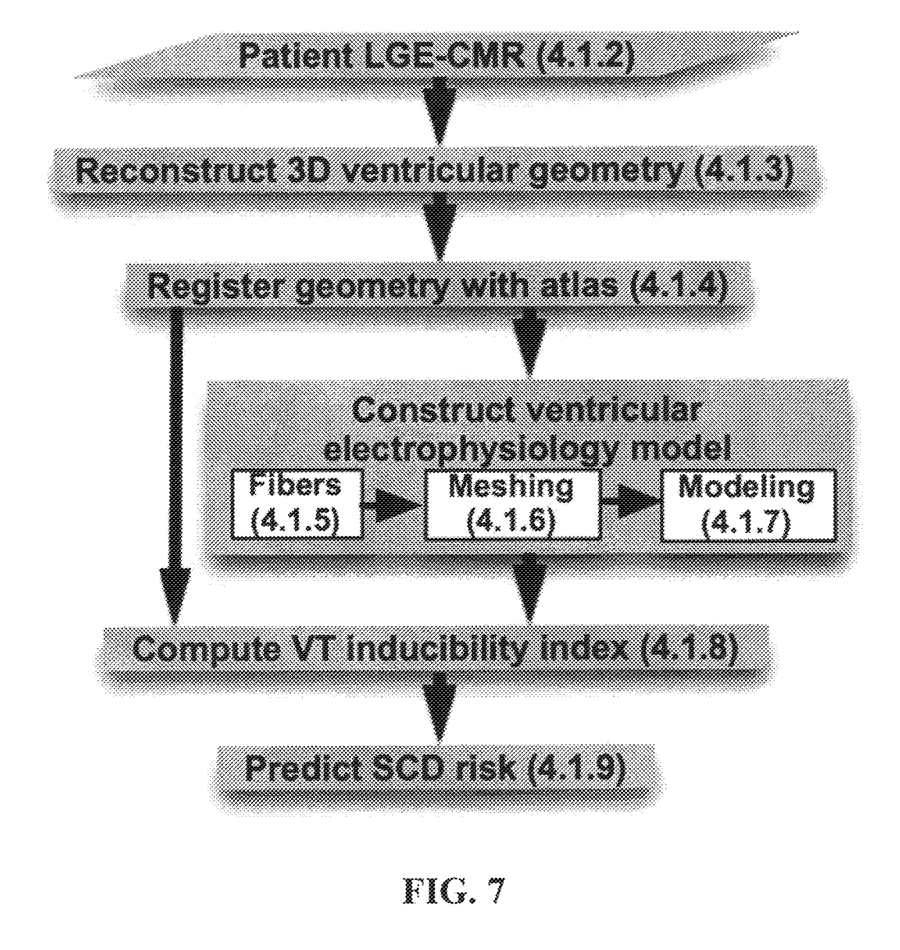
FIG. 7 is a flow chart illustrating some further details that can be used in the method of FIG. 6, according to an embodiment of the current invention.

FIG. 7 is a flowchart illustrating methods according to some embodiments of the current invention. The data are illustrated in a parallelogram, and the processing steps in rectangular blocks. Note that the results of registration of the patient heart geometry with the atlas is used both in the estimation of patient fiber orientations, and automatic placement of PES sites. However, the general concepts of the current invention are not limited to these examples. We have other methods for both fiber estimation and automatic placement of the PES sites Reconstruction of 3D Ventricular and Infarct Geometries from Clinical LGE-CMR Images It is necessary to reconstruct high-resolution (<=1 mm isotropic) 3D geometries of the ventricles and infarct of fibrotic regions for some applications according to an embodiment of the current invention. This is a challenging task, because the clinical LGE-CMR images have poor intensity contrast between myocardial tissue and the rest of the torso, and the image resolution is very low (~2×2×10 $mm^3$). A semi-automatic approach according to an embodiment of the current invention is illustrated in FIGS. 1 and 2 (for a heart with infarction). In each short-axis slice, four smooth contours that represent endocardium and epicardium of LV and RV are semi-automatically drawn. The section of the LV wall that belongs to the septum is then manually identified by placing two landmark points near the RV insertion points. From the contours and insertion points, a 3D geometry of the ventricular structures with desired resolution is constructed, based on a modification of the variational implicit functions strategy proposed by Turk and O'Brien [16]. Validation experiments using ex vivo data have proved that the variational strategy outperforms the alternatives. For more details, see [15].

To reconstruct the 3D infarct geometry, both core and border zone are segmented in each 2D slice using a modified full width half-maximum (FWHM) algorithm (see FIGS. 1A and 1B) [3]. From the segmentations, a high-resolution 3D reconstruction of both zones is obtained via a shape-based binary interpolation method [17] that perfectly fits the 2D data and reconstructs complex geometries (see FIG. 2). The same algorithm is used to segment out fibrotic regions (FIG. 8).

The tools to perform sufficiently detailed 3D reconstructions of ventricles and infarct zones have been developed and demonstrated. These tools have been applied to clinical LGE-CMR images of several patients. A detailed illustration of a reconstruction is shown in FIG. 2.

Automatic Placement of PES Sites

To automatically select PES sites according to some embodiments of the current invention, it is necessary to calculate point-to-point anatomical correspondences between different patient hearts. To this end, the 3D ventricular geometry of a normal human heart was reconstructed from an ex vivo DTMRI image as an "atlas" [14], and the 17 AHA regions as well as locations of the PES sites are manually labeled on it. A total of 19 PES sites, including the RV apex, the point closest to the RV outflow tract, and centers of the endocardial surfaces of each of the 17 AHA segments, are labeled. This particular set of PES sites are chosen because it includes not only the RV sites used in clinical EPS, but also numerous sites that sufficiently sample the LV endocardium while keeping the in silico inducibility test computationally tractable. Anatomically meaningful point-to-point correspondences between the atlas and each patient ventricular geometry are then computed by registering the atlas with the patient geometry using a combination of affine transformation and multi-channel large deformation diffeomorphic metric mapping (MC-LDDMM), with LV chamber, LV free-wall, septum, RV chamber, and RV free-wall as channels [18] (see also [15]). FIGS. 4A-4D illustrate the registration of two heart geometries. For each manually identified PES site on the atlas endocardium, the corresponding point on a patient heart is automatically identified as a PES site.

Estimation of Ventricular Fiber Orientations

Data regarding 3D orientations of myocytes (fiber orientations) are necessary to build the ventricular electrophysiological models for the inducibility studies according to some embodiments of the current invention, because these orientations determine directions of electrical propagation in the heart [14]. However, clinical acquisition of fiber orientations has not been feasible [14]. Accordingly, a computational anatomy-based methodology to estimate fiber orientations of patient hearts whose geometries are reconstructed from clinical images [14] has been developed. The methodology involves registering the geometry of an atlas heart for which fiber orientations are available from DTMRI, with the geometry of a patient heart, and morphing the atlas fiber orientations according to the deformation field available from the registration [14]. Estimated fiber orientations for an example patient geometry reconstructed from clinical LGE-CMR images are shown in FIG. 4. The fiber estimation methodology is sufficiently accurate for in silico VT inducibility studies in post-MI patients according to some embodiments of the current invention. Simulation experiments [14, 19] have demonstrated that outcomes of electrophysiological simulations, including patterns of VTs [14, 20], are insensitive to small changes in fiber orientations, and the reported changes in fiber orientations introduced by inter-subject variability and myocardial infarction are small. The accuracy of estimated orientations is sufficient for SCD risk stratification according to some embodiments of the current invention.

Generation of Ventricular Computational Meshes

Finite element meshes needed for building models of ventricular electrophysiology according to some embodiments of the current invention can be generated using an automatic algorithm [14]. This software generates meshes directly from patient-specific ventricular and infarct geometries reconstructed as described above. Each element in the mesh is labeled with the corresponding tissue type, including normal ventricular myocardium, infarct core, and infarct border zone, to facilitate assignment appropriate electrophysiological properties during simulations. Each element is also assigned with a fiber orientation, estimated as described above. The meshes used in some examples according to an embodiment of the current invention have an average resolution of ~250 μm, which has been shown to be sufficient for cardiac electrophysiological simulations.

Biophysically Detailed Multiscale Electrophysiological Modeling

Modeling methods already implemented and validated by Dr. Trayanova's team, which has pioneered the use of large, multiscale models to understand arrhythmogenesis under various conditions, including ICM and fibrosis [7, 8, 21-26]. Briefly, given the high-resolution mesh of patient ventricles with fiber orientations, built as described above (se e also FIG. 4), the propagation of a wave of transmembrane potential can be simulated by solving a reaction-diffusion partial differential equation (PDE). However, the general concepts of the current invention are not limited to just this one approach. Areaction-diffusion equation coupled to an eliptical equation can also be solved (a bidomain approach). While the latter representation is more complex, it could be somewhat more accurate. Electrophysiological heterogeneities throughout the ventricles, including transmural and apical-basal heterogeneities, are assigned in accordance with human cardiac tissue data. The passive tissue properties are characterized with anisotropic conductivities, the values of which for normal myocardium are derived from literature and adjusted to match typical activation patterns and conduction velocity from experimental studies. The infarct core zone is assumed to be an insulator, and the border zone is modeled with significantly decreased peak ionic conductances and transverse conductivity.

Modeling Fibrosis

Fibrosis is characterized by a progressive thickening of the interstitial matrix, including increased collagen deposition, and subsequent separation of individual myocytes. Therefore, we model regions of fibrosis, segmented from the patient-specific LDE-CMR scans, with decreased conductivity values representing connexin43 (Cx43) downregulation, and increased anisotropy ratios, representing Cx43 lateralization. Collagenous septa in fibrotic lesions are most often aligned with the fiber direction; we thus introduce collagenous septa in this way. Lastly, since increased fibroblast proliferation and phenotype switching as well as heterocellular coupling have been observed in fibrotic tissue, we distribute myofibroblasts, represented by either the model of MacCannell et al or another ionic model of the fibroblast, that electrically couple among themselves and with myocytes, throughout the fibrotic regions of the models. Alternatively, myofibroblasts may exert paracrine influences on the ionic currents of neighboring myocytes, which we also represent.

Computation of in Silico VT Inducibility Index

To assess the VT induciblilty of each patient in silico according to some embodiments of the current invention, PES is applied at the sites described above, on the patient-specific ventricular model built as described above. At each site, the PES is performed via an S1-S2-S3 stimuli protocol, as done in the clinic [4]. If VT is induced following S2 or S3, then the patient heart is labeled as inducible from the corresponding pacing site. If VT is not induced from any of the pacing sites, then the patient heart is assessed as non-inducible. The proportion of the pacing sites from which a VT is induced constitutes the in silico VT inducibility index of a patient.

Statistical Analysis Methods

The in-silico VT inducibility index is compared between high-risk and low-risk patient groups using Wilcoxon rank sum test, with a significance level of $\alpha=0.05$. Correction for multiple comparisons is done using permutation tests. To compute the predictive accuracy of the index, a univariate dichotomous logistic regression with the risk group (high or low) as the binary response variable is performed. To assess the classification efficacy of the regression model, a 10-fold cross-validation scheme is adopted [27]. The accuracy of the classifier, i.e. the percentage of patients correctly classified as high- or low-risk, is assessed with a probability threshold of 0.5. The overall performance of the classifier in identifying low-risk patients is assessed by computing the receiver operating characteristic (ROC) curve that shows the relationship between sensitivity and false positive rate (100%-specificity) for each value of probability cut-off, ranging from 0 to 1 in 0.05 increments [27].

REFERENCES

[1] D. Zipes, A. Camm, M. Borggrefe, A. Buxton, B. Chaitman, M. Fromer, G. Gregoratos, G. Klein, A. Moss, and R. Myerburg, "ACC/AHA/ESC 2006 Guidelines for Management of Patients With Ventricular Arrhythmias and the Prevention of Sudden Cardiac DeathA Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death)," Journal of the American College of Cardiology, vol. 48, no. 5, pp. e247-e346, 2006.

[2] E. C. Stecker and S. S. Chugh, "Prediction of sudden cardiac death: next steps in pursuit of effective methodology," Journal of Interventional Cardiac Electrophysiology, vol. 31, no. 2, pp. 101-107, 2011.

[3] K. C. Wu, G. Gerstenblith, E. Guallar, J. E. Marine, D. Dalal, A. Cheng, E. Marbán, J. A. C. Lima, G. F. Tomaselli, and R. G. Weiss, "Combined Cardiac MRI and C-Reactive Protein Levels Identify a Cohort at Low Risk for Defibrillator Firings and Death," Circulation: Cardiovascular Imaging, vol. 5, no. 2, pp. 178-186, 2012.

[4] K. E. Thomas and P. J. Zimetbaum, "Electrophysiology Study: Indications and Interpretations," in Management of Cardiac Arrhythmias, G. Yan and P. R. Kowey, Eds., 2 ed: Humana Press, 2011.

[5] S. A. Chen, C. E. Chiang, C. T. Tai, C. C. Cheng, C. W. Chiou, S. H. Lee, K. C. Ueng, Z. C. Wen, and M. S. Chang, "Complications of diagnostic electrophysiologic studies and radiofrequency catheter ablation in patients with tachyarrhythmias: an eight-year survey of 3,966 consecutive procedures in a tertiary referral center," American Journal of Cardiology, vol. 77, no. 1, pp. 41-46, 1996.

[6] J. Ng, J. T. Jacobson, J. K. Ng, D. Gordon, D. C. Lee, J. C. Carr, and J. J. Goldberger, "Virtual Electrophysiological Study in a 3-Dimensional Cardiac Magnetic Resonance Imaging Model of Porcine Myocardial Infarction," Journal of Americal College of Cardiology, vol. xx, no. x, p. Published online, 2012.

[7] N. Trayanova, "Whole Heart Modeling: Applications to Cardiac Electrophysiology and Electromechanics," Circulation Research, vol. 108, no. pp. 113-128, 2011.

[8] F. Vadakkumpadan, L. J. Rantner, B. Tice, P. Boyle, A. J. Prassl, E. Vigmond, G. Plank, and N. Trayanova, "Image-Based Models of Cardiac Structure with Applications in Arrhythmia and Defibrillation Studies," Journal of Electrocardiology, vol. 42, no. 2, pp. 157.e1-157.e10, 2009.

[9] J. Relan, P. Chinchapatnam, M. Sermesant, K. Rhode, M. Ginks, H. Delingette, C. A. Rinaldi, R. Razavi, and N. Ayache, "Coupled personalization of cardiac electrophysiology models for prediction of ischaemic ventricular tachycardia," Interface Focus, vol. 1, no. 3, pp. 396-407, 2011.

[10] M. F. Beg, P. A. Helm, E. McVeigh, M. I. Miller, and R. L. Winslow, "Computational Cardiac Anatomy Using MRI," Magnetic Resonance in Medicine, vol. 52, no. 5, pp. 1167-1174, 2004.

[11] M. Sermesant, R. Chabiniok, P. Chinchapatnam, T. Mansi, F. Billet, P. Moireau, J. M. Peyrat, K. Wong, J. Relan, K. Rhode, M. Ginks, P. Lambiase, H. Delingette, M. Sorine, C. A. Rinaldi, D. Chapelle, R. Razavi, and N. Ayache, "Patient-specific electromechanical models of the heart for the prediction of pacing acute effects in CRT: a preliminary clinical validation," Medical Image Analysis, vol. 16, no. 1, pp. 201-215, 2012.

[12] J. Aguado-Sierra, A. Krishnamurthy, C. Villongco, J. Chuang, E. Howard, M. J. Gonzales, J. Omens, D. E. Krummen, S. Narayan, R. C. Kerckhoffs, and A. D. M. AD., "Patient-specific modeling of dyssynchronous heart failure: a case study," Progress in Biophysics and Molecular Biology, vol. 107, no. 1, pp. 147-155, 2011.

[13] S. C. Hammill, M. S. Kremers, L. W. Stevenson, P. A. Heidenreich, C. M. Lang, J. P. Curtis, Y. Wang, C. I. Berul, A. H. Kadish, S. M. Al-Khatib, I. L. Pina, M. N. Walsh, M. J. Mirro, B. D. Lindsay, M. R. Reynolds, K. Pontzer, L. Blum, F. Masoudi, J. Rumsfeld, and R. G. Brindis, "Review of the Registry's Fourth Year, Incorporating Lead Data and Pediatric ICD Procedures, and Use as a National Performance Measure," Heart Rhythm, vol. 7, no. 9, pp. 1340-1345, 2010.

[14] F. Vadakkumpadan, H. Arevalo, C. Ceritoglu, M. Miller, and N. Trayanova, "Image-Based Estimation of Ventricular Fiber Orientations for Personalized Modeling of Cardiac Electrophysiology," IEEE Transactions on Medical Imaging, vol. 31, no. 5, pp. 1051-1060, 2012. Fijoy Vadakkumpadan, PhD Page 13

[15] F. Vadakkumpadan, N. Trayanova, L. Younes, and K. C. Wu, "Left-Ventricular Shape Analysis for Predicting Sudden Cardiac Death Risk," Proc. Engineering in Medicine and Biology Society San Diego, 2012, In press.

[16] G. Turk and J. O'Brien, "Shape Transformation Using Variational Implicit Functions," Proc. SIGGRAPH, 1999, pp. 335-342.

[17] S. P. Raya and J. K. Udupa, "Shape-based interpolation of multidimensional objects," IEEE Transactions on Medical Imaging, vol. 9, no. 1, pp. 32-42, 1990.
[18] C. Ceritoglu, K. Oishi, X. Li, M. C. Chou, L. Younes, M. Albert, C. Lyketsos, P. C. v. Zijl, M. I. Miller, and S. Mori, "Multi-contrast large deformation diffeomorphic metric mapping for diffusion tensor imaging," Neuroimage, vol. 47, no. 2, pp. 618-627, 2009.
[19] J. D. Bayer, R. C. Blake, G. Plank, and N. A. Trayanova, "A Novel Rule-Based Algorithm for Assigning Myocardial Fiber Orientation to Computational Heart Models," Annals of Biomedical Engineering, no. p. Published online, 2012.
[20] H. J. Arevalo, A. J. Prassl, G. Plank, P. Helm, H. Halperin, and N. A. Trayanova, "Model of the infarcted canine heart predicts arrhythmia generation from specific cardiac geometry and scar distribution," Heart Rythm, no. 2008.
[21] H. Arevalo, B. Rodriguez, and N. Trayanova, "Arrhythmogenesis in the Heart: Multiscale Modeling of the Effects of Defibrillation Shocks and the Role of Electrophysiological Heterogeneity," Chaos, vol. 17, no. 1, p. 015103, 2007.
[22] B. M. Tice, B. Rodriguez, J. Eason, and N. Trayanova, "Mechanistic Investigation into the Arrhythmogenic Role of Transmural Heterogeneities in Regional Ischaemia Phase 1a," Europace, vol. 6, no. pp. vi46-58, 2007.
[23] T. Ashihara, J. Constantino, and N. A. Trayanova, "Tunnel Propagation of Postshock Activations as a Hypothesis for Fibrillation Induction and Isoelectric Window," Circulation Research, vol. 102, no. 6, pp. 737-745, 2008.
[24] X. Jie, V. Gurev, and N. Trayanova, "Mechanisms of mechanically induced spontaneous arrhythmias in acute regional ischemia," Circulation Research, vol. 106, no. 1, pp. 185-192, 2010.
[25] E. Vigmond, F. Vadakkumpadan, V. Gurev, H. Arevalo, M. Deo, G. Plank, and N. Trayanova, "Towards predictive modelling of the electrophysiology of the heart.," Experimental Physiology, vol. 94, no. 5, pp. 563-77, 2009.
[26] G. Plank, L. Zhou, J. L. Greenstein, G. Plank, L. Zhou, J. L. Greenstein, S. Cortassa, R. L. Winslow, B. O'Rourke, and N. A. Trayanova, "From mitochondrial ion channels to arrhythmias in the heart: computational techniques to bridge the spatio-temporal scales," Philosophical Transactions Series A, Mathematical, Physical, and Engineering Sciences, vol. 366, no. 1879, pp. 3381-3409, 2008.
[27] C. Soneson, M. F. M, Y. Zhou, V. Denisov, J. S. Paulsen, D. K. D, and A. Petersén, "Early changes in the hypothalamic region in prodromal Huntington disease revealed by MRI analysis," Neurobiology of Disease, vol. 40, no. 3, pp. 531-543, 2010.
[28] L. Y. Hsu, A. Natanzon, P. Kellman, G. A. Hirsch, A. H. Aletras, and A. E. Arai, "Quantitative myocardial infarction on delayed enhancement MRI. Part I: Animal validation of an automated feature analysis and combined thresholding infarct sizing algorithm," Journal of Magnetic Resonance Imaging, vol. 23, no. 3, pp. 298-308, 2006.
[29] S. Kels and N. Dyn, "Reconstruction of 3D objects from 2D cross-sections with the 4-point subdivision scheme adapted to sets," Computers and Graphics, vol. 35, no. pp. 741-746, 2011.
[30] A. B. Albu, T. Beugeling, and D. Laurendeau, "A morphology-based approach for interslice interpolation of anatomical slices from volumetric images," IEEE Transactions on Biomedical Engineering, vol. 55, no. 8, pp. 2022-2038, 2008.

The above provides some examples according to particular embodiments of the current invention. The broad concepts of the current invention are not limited to only these particular examples.

The three-dimensional imaging data can be MRI data as described in the examples above. However, the broad concepts of the current invention are not limited to that particular example. The three-dimensional imaging data can be can be at least one of magnetic resonance imaging (MRI), computed tomography (CT), positron emission tomography (PET), ultrasound, or nuclear tracer three-dimensional imaging data, for example. The simulating can further include receiving additional patient-specific data in addition to the three-dimensional imaging data. For example, some embodiments can include receiving at least one of biopsy data, electrocardiogram data, recorded data from an implantable device (pace maker, defibrillator, etc.), or invasive electrical mapping data (e.g., endoscopic).

The simulating at least one of electrophysiological or electromechanical activity of at least the portion of the patient's heart can include constructing a geometric model of the portion of the patient's heart. The geometric model can include normal tissue regions and remodeled tissue regions that are determined for the patient using the three-dimensional imaging data. The term "remodeled tissue" can include infarct scar, infarct border (gray) zone, fibrosis, or other disease-related structural, electrophysiological or contractile changes in the heart. The simulating can further include estimating tissue fiber orientations in the geometric model of the portion of the patient's heart. The estimation of fiber orientations can be done in a variety of ways. For example, the fiber orientations can be calculated using a Laplace-Dirichlet method to define the local transmural and apicobasal axes at each spatial location in the ventricles, (J. D. Bayer, R. Blake, G. Plank, Trayanova N, Novel rule based algorithm for assigning myocardial fiber orientation to computation heart models. *Ann Biomed Eng.*, 40:2243-2254, 2012, the entire contents of which are incorporated herein by reference). Another approach could utilize pre-compiled data (i.e., atlas data), which can be mapped into the specific size and shape of the patient's heart (Image-Based Estimation of Ventricular Fiber Orientations for Personalized Modeling of Cardiac Electrophysiology, Vadakkumpadan F, Arevalo H, Ceritoglu C, Miller M, Trayanova N., IEEE Trans Med Imaging., 31:1051-1060, 2012, the entire contents of which are incorporated herein by reference).

The embodiments discussed in this specification are intended to explain concepts of the invention. However, the invention is not intended to be limited to the specific terminology selected and the particular examples described. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A computer-implemented method of determining a likelihood of an occurrence of a cardiac arrhythmia in a living patient, comprising:

receiving contrast-enhanced three-dimensional MRI or CT data that includes said living patient's heart;

segmenting said contrast-enhanced three-dimensional MRI or CT data of said living patient's heart to obtain three-dimensional heart image data;

segmenting said three-dimensional heart image data into a plurality of different tissue types of said heart based on said contrast-enhanced three-dimensional MRI or CT data, said plurality of different tissue types including a normal tissue region, a scar tissue region, and a transition zone region, said transition zone region including an infarct border zone tissue region;

constructing a whole-heart model of said living patient's heart, said constructing said model comprising:

creating a finite element mesh using the segmented three-dimensional MRI or CT data to provide a geometrical representation of said patient's heart, the finite element mesh comprising a plurality of volume elements, wherein the volume elements each represent a volume having an edge length in a range of about 300-400 microns;

determining a fiber orientation in each of the volume elements based on information from both geometry and fiber images of an atlas human heart and without fiber images of the patient's heart; and assigning electrophysiological parameters to each of the volume elements taking into account the fiber orientations and the type of tissue where the corresponding volume element is located;

solving, at each element of the said finite elements mesh of the living patient's heart with the said determined heart fiber orientations, the equations describing electrical signal propagation through the heart, together with the local equations describing cardiac cell's ion transport across the membrane;

executing the said solving of electrical signal propagation in the living patient's heart to simulate a response of said patient's heart to each of a plurality of stimulations from a plurality of locations within said patient's heart;

classifying each simulation outcome for each stimulation as one resulting in a cardiac arrhythmia or not resulting in a cardiac arrhythmia;

calculating a likelihood index based on results of said classifying; and comparing said likelihood index to a predetermined threshold such that exceeding said predetermined threshold indicates that said living patient is a candidate for an implantable cardioverter defibrillator.

2. A method of determining a likelihood of an occurrence of a cardiac arrhythmia in a patient according to claim 1, wherein said calculating said likelihood index is calculating a ratio of number of simulation outcomes resulting in a classification of cardiac arrhythmia divided by total number of simulation outcomes.

3. A method of determining a likelihood of an occurrence of a cardiac arrhythmia in a patient according to claim 1, wherein said predetermined threshold is 0.5.

4. A method of determining a likelihood of an occurrence of a cardiac arrhythmia in a patient according to claim 1, wherein said plurality of stimulations are electrical stimulations.

5. A method of determining a likelihood of an occurrence of a cardiac arrhythmia in a patient according to claim 1, further comprising:

receiving additional patient-specific data that includes at least one of biopsy data, electrocardiogram data, recorded data from an implantable device, or invasive electrical mapping data, wherein said simulating uses said additional patient-specific data.

6. A method of determining a likelihood of an occurrence of a cardiac arrhythmia in a patient according to claim 1, wherein said tissue regions comprise at least one of infarction or fibrosis.

7. A non-transitory computer-readable medium for determining a likelihood of an occurrence of a cardiac arrhythmia in a living patient, said computer-readable medium comprising non-transitory computer-executable code which, when executed by a computer, causes the computer to:

receive contrast-enhanced three-dimensional MRI or CT data that includes said living patient's heart;

segment said contrast-enhanced three-dimensional MRI or CT data of said living patient's heart to obtain three-dimensional heart image data;

segment said three-dimensional heart image data into a plurality of different tissue types of said heart based on said contrast-enhanced three-dimensional MRI or CT data, said plurality of different tissue types including a normal tissue region, a scar tissue region, and a transition zone region, said transition zone region including an infarct border zone tissue region;

construct a whole-heart model of said living patient's heart, said constructing said model comprising:

creating a finite element mesh using the segmented three-dimensional data to provide a geometrical representation of said patient's heart, the finite element mesh comprising a plurality of volume elements, wherein the volume elements each represent a volume having an edge length in a range of about 300-400 microns;

determining a fiber orientation in each of the volume elements based on information from both geometry and fiber images of an atlas human heart and without fiber images of the patient's heart; and assigning electrophysiological parameters to each of the volume elements taking into account the fiber orientations and the type of tissue where the corresponding volume element is located;

solving, at each element of the said finite elements mesh of the living patient's heart with the said determined heart fiber orientations, the equations describing electrical signal propagation through the heart, together with the local equations describing cardiac cell's ion transport across the membrane;

executing the said solving of electrical signal propagation in the living patient's heart to simulate a response of said patient's heart to each of a plurality of stimulations from a plurality of locations within said patient's heart;

classify each simulation outcome for each stimulation as one of a normal heart rhythm or a cardiac arrhythmia;

calculate a likelihood index based on results of said classifying; and compare said likelihood index to a predetermined threshold such that exceeding said predetermined threshold indicates that said living patient is a candidate for an implantable cardioverter defibrillator.

8. A non-transitory computer-readable medium for determining a likelihood of an occurrence of a cardiac arrhythmia in a patient according to claim 7, wherein said providing said likelihood index includes calculating a ratio of number of simulation outcomes resulting in a classification of cardiac arrhythmia divided by total number of simulation outcomes.

9. A non-transitory computer-readable medium for determining a likelihood of an occurrence of a cardiac arrhythmia in a patient according to claim 7, wherein said predetermined threshold is 0.5.

10. A non-transitory computer-readable medium for determining a likelihood of an occurrence of a cardiac arrhythmia in a patient according to claim 7, wherein said plurality of stimulations are electrical stimulations.

11. A non-transitory computer-readable medium for determining a likelihood of an occurrence of a cardiac arrhythmia in a patient according to claim 7, wherein said computer-executable code further causes said computer to:
receive additional patient-specific data that includes at least one of biopsy data, electrocardiogram data, recorded data from an implantable device, or invasive electrical mapping data,
wherein said simulating uses said additional patient-specific data.

12. A non-transitory computer-readable medium for determining a likelihood of an occurrence of a cardiac arrhythmia in a patient according to claim 7, wherein said tissue regions comprise at least one of infarction or fibrosis.

13. A system for determining a likelihood of an occurrence of a cardiac arrhythmia in a living patient comprising a data processor, wherein said data processor is configured to:
receive contrast-enhanced three-dimensional MRI or CT data that includes said living patient's heart;
segment said contrast-enhanced three-dimensional MRI or CT data of said living patient's heart to obtain three-dimensional heart image data;
segment said three-dimensional heart image data into a plurality of different tissue types of said heart based on said contrast-enhanced three-dimensional data, said plurality of different tissue types including a normal tissue region, a scar tissue region, and a transition zone region, said transition zone region including an infarct border zone tissue region;
construct a whole-heart model of said living patient's heart, said constructing said model comprising:
creating a finite element mesh using the segmented three-dimensional data to provide a geometrical representation of said patient's heart, the finite element mesh comprising a plurality of volume elements, wherein the volume elements each represent a volume having an edge length in a range of about 300-400 microns;
determining a fiber orientation in each of the volume elements based on information from both geometry and fiber images of an atlas human heart and without fiber images of the patient's heart; and
assigning electrophysiological parameters to each of the volume elements taking into account the fiber orientations and the type of tissue where the corresponding volume element is located;
solving, at each element of the said finite elements mesh of the living patient's heart with the said determined heart fiber orientations, the equations describing electrical signal propagation through the heart, together with the local equations describing cardiac cell's ion transport across the membrane;
executing the said solving of electrical signal propagation in the living patient's heart to simulate a response of said patient's heart to each of a plurality of stimulations from a plurality of locations within said patient's heart;
classify each simulation outcome for each stimulation as one of a normal heart rhythm or a cardiac arrhythmia;
calculate a likelihood index based on results of said classifying; and
compare said likelihood index to a predetermined threshold such that exceeding said predetermined threshold indicates that said living patient is a candidate for an implantable cardioverter defibrillator.

14. A system for determining a likelihood of an occurrence of a cardiac arrhythmia in a patient according to claim 13, wherein said determining said likelihood index includes calculating a ratio of number of simulation outcomes resulting in a classification of cardiac arrhythmia divided by total number of simulation outcomes.

15. A system for determining a likelihood of an occurrence of a cardiac arrhythmia in a patient according to claim 13, wherein said predetermined threshold is 0.5.

16. A system for determining a likelihood of an occurrence of a cardiac arrhythmia in a patient according to claim 13, wherein said plurality of stimulations are electrical stimulations.

17. A system for determining a likelihood of an occurrence of a cardiac arrhythmia in a patient according to claim 13, wherein said data processor is further configured to:
receive additional patient-specific data that includes at least one of biopsy data, electrocardiogram data, recorded data from an implantable device, or invasive electrical mapping data,
wherein said simulating uses said additional patient-specific data.

18. A system for determining a likelihood of an occurrence of a cardiac arrhythmia in a patient according to claim 13, wherein said tissue regions comprise at least one of infarction or fibrosis.

19. A method of determining a likelihood of an occurrence of a cardiac arrhythmia in a patient according to claim 1, wherein said plurality of locations comprise a left ventricle and a right ventricle of said living patient's heart.

20. A non-transitory computer-readable medium for determining a likelihood of an occurrence of a cardiac arrhythmia in a patient according to claim 7, wherein said plurality of locations comprise a left ventricle and a right ventricle of said living patient's heart.

21. A system for determining a likelihood of an occurrence of a cardiac arrhythmia in a patient according to claim 13, wherein said plurality of locations comprise a left ventricle and a right ventricle of said living patient's heart.

22. A method of determining a likelihood of an occurrence of a cardiac arrhythmia in a patient according to claim 1, wherein said assigning said fiber orientations is based on predetermined rules of the patient's heart.

23. A method of determining a likelihood of an occurrence of a cardiac arrhythmia in a patient according to claim 1, wherein the volume elements are tetrahedra-shaped.

24. A non-transitory computer-readable medium for determining a likelihood of an occurrence of a cardiac arrhythmia in a patient according to claim 7, wherein said assigning said fiber orientations is based on predetermined rules of the patient's heart.

25. A non-transitory computer-readable medium for determining a likelihood of an occurrence of a cardiac arrhythmia in a patient according to claim 7, wherein the volume elements are tetrahedra-shaped.

26. A system for determining a likelihood of an occurrence of a cardiac arrhythmia in a patient according to claim 13, wherein said assigning said fiber orientations is based on predetermined rules of the patient's heart.

27. A system for determining a likelihood of an occurrence of a cardiac arrhythmia in a patient according to claim 13, wherein the volume elements are tetrahedra-shaped.

28. A method of determining a likelihood of an occurrence of a cardiac arrhythmia in a patient according to claim 1, further comprising implanting an implantable cardioverter-defibrillator into the living patient in response to said likelihood index.

\* \* \* \* \*